(12) United States Patent
Herz et al.

(10) Patent No.: US 7,867,485 B2
(45) Date of Patent: *Jan. 11, 2011

(54) METHOD FOR PREVENTING OR TREATING THE DEVELOPMENT OF RESPIRATORY ALLERGIES

(75) Inventors: Udo Herz, Kirchhain (DE); Nicole Bluemer, Marburg (DE); Harald Renz, Marburg (DE); Holger Garn, Marburg (DE)

(73) Assignee: Mead Johnson Nutrition Company, Evansville, IN (US)

( * ) Notice: Subject to any disclaimer, the term of this patent is extended or adjusted under 35 U.S.C. 154(b) by 643 days.

This patent is subject to a terminal disclaimer.

(21) Appl. No.: 11/875,385

(22) Filed: Oct. 19, 2007

(65) Prior Publication Data

US 2008/0118483 A1 May 22, 2008

Related U.S. Application Data

(60) Division of application No. 11/144,287, filed on Jun. 3, 2005, now Pat. No. 7,303,745, which is a continuation of application No. 11/106,792, filed on Apr. 15, 2005, now abandoned.

(51) Int. Cl.
*A01N 63/00* (2006.01)
(52) U.S. Cl. .................................... 424/93.45
(58) Field of Classification Search ........... None
See application file for complete search history.

(56) References Cited

U.S. PATENT DOCUMENTS

| | | | |
|---|---|---|---|
| 5,840,318 A | 11/1998 | Marshall et al. | |
| 6,203,797 B1 | 3/2001 | Perry | |
| 6,461,607 B1 | 10/2002 | Farmer | |
| 6,613,549 B2 | 9/2003 | Reid et al. | |
| 6,696,057 B1 | 2/2004 | Bojrab | |
| 7,303,745 B2 * | 12/2007 | Herz et al. ............... | 424/93.45 |
| 2003/0031659 A1 | 2/2003 | Farmer | |
| 2003/0118571 A1 | 6/2003 | Reid et al. | |
| 2003/0180260 A1 | 9/2003 | Clancy et al. | |
| 2003/0180272 A1 | 9/2003 | Isolauri et al. | |
| 2003/0215467 A1 | 11/2003 | Collins et al. | |
| 2004/0057965 A1 | 3/2004 | Clancy et al. | |
| 2004/0115178 A1 | 6/2004 | Schiffrin et al. | |
| 2004/0147010 A1 | 7/2004 | Vidal et al. | |
| 2004/0197304 A1 | 10/2004 | Chen et al. | |
| 2004/0219157 A1 | 11/2004 | Rochat et al. | |
| 2004/0265291 A1 | 12/2004 | Drake et al. | |
| 2006/0018890 A1 | 1/2006 | Isolauri et al. | |

FOREIGN PATENT DOCUMENTS

| | | |
|---|---|---|
| EP | 1364586 A1 | 5/2002 |
| JP | 2002 332242 A | 11/2002 |
| WO | WO 97/00078 | 1/1997 |
| WO | WO 98/36745 A2 | 8/1998 |
| WO | WO 00/35443 A1 | 6/2000 |
| WO | WO 01/32836 A1 | 5/2001 |

OTHER PUBLICATIONS

U.S. Appl. No. 11/875,329, filed Jun. 5, 2008, Herz, et al.
U.S. Appl. No. 11/875,418, filed May 22, 2008, Herz, et al.
U.S. Appl. No. 11/875,441, filed Apr. 10, 2008, Herz, et al.
U.S. Appl. No. 11/875,474, filed May 22, 2008, Herz, et al.
Agostoni, C, et al., *Probiotic Bacteria in Dietetic Products for Infants: A Commentary by the ESPGHAN Committee on Nutrition*, Journal of Pediatric Gastroenterology and Nutrition, Apr. 2004, vol. 38, pp. 365-374.
Bai, Al-Ping, et al., *Probiotics inhibit TNF-a-induced interleukin-8 secretion of HT29 cells*, World Journal of Gastroenterology, 2004, vol. 10(3), pp. 455-457.
Article *Bacterial DNA Reduces Inflammation in Mice*, IBDanswers: Crohn's Disease, Colitis and Inflammatory Bowel Disease—Bacterial DNA, 2004. [Online] http://www.ibdanswers.com/Members/ScooterGirl/probiotics-2004.
Arvola, T, et al., *Prophylactic Lactobacillus GG Reduces Antibiotic-Associated Diarrhea in Children With Respiratory Infections: A Randomized Study*, Pediatrics, 1999, vol. 104, No. 5, pp. 1-4.
Auestad, N, et al., *Milk-substitutes comparable to rat's milk; their preparation, composition and impact on development and metabolism in the artificially reared rat*, Br J Nutr, 1989, 61:p. 495-518.
Breese, E, et al., *TNFa Secreting Cells in Normal and Diseased Human Intestine*, Adv Exp Med Biol, 1995; 37aB: p. 821-824.
Carlson, SE, et al., *Lower Incidence of Necrotizing Enterocolitis in Infants Fed a Preterm Formula with Egg Phospholipids*, Pediatric Research, Williams and Wilkins, vol. 44, No. 4, Oct. 1998, pp. 491-498.
Castagliuolo, I, et al., *Clostridium difficile Toxin A Stimulates Macrophage-Inflammatory Protein-2 Production in Rat Intestinal Epithelial Cells*[1], J Immunol, 1998, 160(12): p. 6039-6045.
Cerra, FB, et al., *Septic Autocannibalism—A Failure of Exogenous Nutritional Support*, Ann Surg 1980; 192: p. 570-580.
Claud, EC, et al., *Hypothesis: inappropriate colonization of the premature intestine can cause neonatal necrotizing enterocolitis*, The FASEB Journal, 2001, vol. 15, pp. 1398-1403. [Online] http://www.fasebj.org.cgi.content/full/15/8/1398.
Claud, Erika C, et al., *Developmentally regulated IkB expression in intestinal epithelium and susceptibility to flagellin-induced inflammation*, PNAS, May 11, 2004, vol. 101, No. 19, pp. 7404-7408. [Online] http://www.pnas.org/cgi/content/full/101/19/7404.

(Continued)

Primary Examiner—Herbert J. Lilling
(74) Attorney, Agent, or Firm—Waddey & Patterson, P.C.; James R. Cartiglia

(57) ABSTRACT

The present invention is directed to a novel method for preventing or treating the development of respiratory allergies. The method comprises prenatal and/or postnatal administration of a therapeutically effective amount of LGG.

16 Claims, 9 Drawing Sheets

OTHER PUBLICATIONS

Collins, M David, et al., *Probiotics, prebiotics, and synbiotics: approaches for modulating the microbial ecology of the gut*[1,2], The American Journal of Clinical Nutrition, May 1999, vol. 69, No. 5, 1052S-1057S. [Online] http://www.ajcn.org/cgi/content/full/69/5/1052S.

Daig, RT, et al., *Increased interleukin 8 expression in the colon mucosa of patients with inflammatory bowel disease*, Gut, 1996; 38: p. 216-222.

Dani, C, et al., *Probiotics Feeding in Prevention of Urinary Tract Infection, Bacterial Sepsis and Necrotizing Enterocolitis in Preterm Infants*, Biol Neonate, 2002; 82: p. 103-108.

Das, Undurti N, *A Perinatal Strategy to Prevent Coronary Heart Disease*, Nutrition (Burbank, Los Angeles County, Calif), Nov.-Dec. 2003, vol. 19, No. 11-12, Nov. 2003, pp. 1022-1027.

De Bont, ES, et al., *Diagnostic value of plasma levels of tumor necrosis factor a (TNFa) and interleukin-6 (IL-6) in newborns with sepsis*, Acta Paediatr Jpn, 1994; 83: p. 696-699.

De Vrese, M, et al., *Probiotics and non-intestinal infectious conditions*, British Journal of Nutrition, 2002, United Kingdom, vol. 88, Suppl 1, 2002, pp. S59-S66.

Deitch, EA et al., *Evidence Favoring the Role of the Gut as a Cytokine-generating Organ in Rats Subjected to Hemorrhagic Shock*, Shock, 1994; 1(2): p. 141-145.

Deplancke, B et al., *Microbial modulation of innate defense: goblet cells and the intestinal mucus layer*[1-3], Am J Clin Nutr 2001; 73 (Suppl): 1131-1141.

*Diagnosis and Management of Acute Otitis Media*, Clinical Practice Guideline by American Academy of Pediatrics, American Academy of Family Physicians.

Dudley, DJ, *Pre-term labor: an intra-uterine inflammatory response syndrome?*[1], J Reproductive Immunology, 1997; 36: p. 93-109.

Duffy, L et al., *Exclusive Breastfeeding Protects Against acterial Colonization and Day Care Exposure to Otitis Media*, Pediatrics, 1997, vol. 100, No. 4, pp. 1-8. [Online] http://www.pediatrics.org/cgi/content/full/100/4/e7.

Duffy, LC, *Interactions Mediating Bacterial Translocation in the Immature Intestine*[1,2], J Nutr, 2000; 130: p. 432-436.

Mattsson, Eva et al., *Highly Purified Lipoteichoic Acid from Staphylococcus aureus Induces Procoagulant Activity and Tissue Factor Expression in Human Monocytes but Is a Weak Inducer in Whole Blood: Comparison with Peptidoglycan*, Infection and Immunity, Jul. 2004, vol. 72, No. 7, pp. 4322-4326. [Online] http://iai.asm.org/cgi/content/full/72/7/4322.

Fischer, CP et al., *Hepatic Uptake of Glutamine and Other Amino Acids During Infection and Inflammation*, Shock, 1995; 3(5): p. 315-22.

Fong, YM et al., *The Acute Splanchnic and Peripheral Tissue Metabolic Response to Endotoxin in Humans*, J Clin Invest, 1990; 85: p. 1896-1904.

Ghisolfi, J et al., *Infant Formula Supplemented With Probiotics or Prebiotics: Never, Now, or Someday?*, Journal of Pediatric Gastroenterology and Nutrition, 2002; 35(4): p. 467-468.

Gluck, U et al., *Ingested probiotics reduce nasal colonization with pathogenic bacteria (Staphylococcus aureus, Streptococcus pneumoniae, and B-hemoltic streptococci)*[-3], American Journal of Clinical Nutrition, 2003, vol. 77, pp. 517-520.

Reid, Gregor, et al., *Potential Uses of Probiotics in Clinical Practice*, Clinical Microbiology Reviews, Oct. 2003, vol. 16(4), pp. 658-672. [Online] http://www.pubmedcentral.nih.gov/articlerender.fcgi?artid=207122.

Hall, WG, *Weaning and Growth of Artificially Reared Rats*, Science, 1975; 190(4221): p. 1313-1315.

Haller, D et al., *Non-pathogenic bacteria elicit a differential cytokine response by intestinal epithelial cell/leucocyte co-cultures*, Gut, 2000, 47(1): p. 79-87.

Harmsen, HJ et al., *Analysis of Intestinal Flora Development in Breast-Fed and Formula-Fed Infants by Using Molecular Identification and Detection Methods*, J Pediatr Gastroenterol Nutr 2000; 30(1), p. 61-67.

Harris, ED, *Differential PCR and DNA Microarrays: The Modern Era of Nutritional Investigations*, Nutrition, 2000; 16(7-8): p. 714-5.

*Health benefits of Lactobacillus GG*, Valio Ltd. 2003.

Hooper, LV et al., *How Host-Microbial Interactions Shape the Nutrient Environment of the Mammalian Intestine*, Annu Rev Nutr 2002; 22: p. 283-307.

Hori, T et al., *Effect of Intranasal Administration of Lactobacillus casei Shirota on Influenza Virus Infection of Upper Respiratory Tract in Mice*, Clinical and Diagnostic Laboratory Immunology, American Society for Microbiology, US, vol. 8, No. 3, May 2001, pp. 593-597.

Hoyos, AB, *Reduced Incidence of Necrotizing Enterocolitis Associated with Enteral Administration of Lactobacillus acidophilus and Bifidobacterium infantis to Neonates in an Intensive Care Unit*, Int J Infect Dis, 1999; 3(4): p. 197-202.

International Search Report of the International Searching Authority for application No. PCT/US2006/010321, International filing Mar. 22, 2006.. Date of mailing Aug. 14, 2006.

International Search Report of the International Searching Authority for application No. PCT/US2006/010415, International filing date Mar. 22, 2006. Date of mailing Aug. 14, 2006.

Isolauri, E et al., *Probiotics: effects on immunity*[1-3], American Journal Clinical Nutrition, 2001; vol. 73(suppl), pp. 444S-450S.

Isolauri, E et al., *Probiotics in the management of atopic eczema*, Clinical and Experimental Allergy, 2000, vol. 30, pp. 1604-1610.

Isolauri, E, *Probiotics in human disease*[1,2,3], American Journal of Clinical Nutrition, Jun. 2001, vol. 73, No. 6, pp. 1142S-1146S. [Online] http://www.ajcn.org/cgi/content/full/73/6/11428S.

Isolauri, E, *Probiotics in the treatment and prevention of allergies*, Monatsschr Kinderheilkd, 2003, vol. 151(Suppl 1), pp. S27-S30.

Jiang, J et al., *Kinetics of Endotoxin and Tumor Necrosis Factor Appearance in Portal and Systemic Circulation After Hemorrhagic Shock in Rats*, Ann Surg 1995, 221(1): p. 100-106.

Juntunen, M et al., *Adherence of Probiotic Bacteria to Human Intestinal Mucus in Healthy Infants and during Rotavirus Infection*, Clinical and Diagnostic Laboratory Immunology, Mar. 2001, vol. 8, No. 2, pp. 293-296. [Online] http://cdii.asm.org/cgi/content/full/8/2/293.

Kaila, M et al., *Fatty acids in substitute formulas for cow's milk allergy*, Allergy, Munskgaard, vol. 54, No. 1, 1999, pp. 74-77.

Kankaanpaa, P et al., *Influence of probiotic supplemented infant formula on composition of plasma lipids in atopic infants*, Journal of Nutritional Biochemistry, 2002, vol. 13, pp. 365-369.

Vidal, Karine et al., *Lipoteichoic Acids from Lactobacillus johnsonii Strain La1 and Lactobacillus acidophilus Strain La10 Antagonize the Responsiveness of Human Intestinal Epithelial HT29 Cells to Lipopolysaccharide and Gram-Negative Bacteria*, Infection and Immunity, Apr. 2002, vol. 70, No. 4, pp. 2057-2064. [Online] http://iai.asm.org/cgi/content/full/70/4/2057.

Kimura, K et al., *Analysis of Fecal Populations of Bifidobacteria and Lactobacilli and Investigation of the Immunological Responses of Their Human Hosts to the Predominant Strains*, Applied and Environmental Microbiology, 1997, vol. 63, No. 9, pp. 3394-3398.

Kirjavainen, PV et al., *Aberrant composition of gut microbiota of allergic infants: a target of bifidobacterial therapy at weaning?*, Gut Journal, 2002, vol. 51, pp. 51-55. [Online] http://www.gutinl.com.

Lu, L et al., *Pathologic and physiologic interactions of bacteria with the gastrointestinal epithelium*[1-3], Am J Clin Nutr, 2001; 73(suppl): p. 1124-30.

Saxelin, Maija, *LGG Summatim*, Valio LTD, R&D, Helsinki, Finland, 2002, Second, updated Edition, pp. 1-59.

Mainous, MR et al., *The Gut: A Cytokine-Generating Organ in Systemic Inflammation?*, Shock, 1995; 4: p. 193-199.

Mainous, MR et al., *Nutritional Support of the Gut: How and Why*, New Horiz, 1995; 2(2): p. 193-201.

Majamaa, H et al., *Probiotics: A novel approach in the management of food allergy*, Journal of Allergy and Clinical Immunology, Mosby-Yearly Book, Inc, US, vol. 99, No. 2, 1997, pp. 179-185.

Marteau, Philippe R et al., *Protection from gastrointestinal diseases with the use of probiotics*[1,2,3], American Journal of Clinical Nutrition, Feb. 2001, vol. 73, No. 2, pp. 430S-436S. [Online] http://www.ajcn.org/cgi/content/full/73/2/430S.

Matsuguchi, Tetsuya et al., *Lipoteichoic Acids from Lactobacillus Strains Elicit Strong Tumor Necrosis Factor Alpha-Inducing Activities in Macrophages through Toll-Like Receptor 2*, Clinical and Diagnostic Laboratory Immunology, Mar. 2003, vol. 10, No. 2, pp. 259-266. [Online] http://cdli.asm.org/cgi/content/full/10/2/259.
Mihrshahi, Seema et al., *Eighteen-month outcomes of house dust mite avoidance and dietary fatty acid modification in the Childhood Asthma Prevention Study (CAPS)*, Journal of Allergy and Clinical Immunology, vol. 111, No. 1, Jan. 2003, pp. 162-168.
Millar, M et al., *Probiotics for preterm infants?*, Arch Dis Child Fetal Neonatal Education, 2003, vol. 88, pp. F354-F358. [Online] http://archdischild.com.
Morecroft, JA et al., *Necrotizing enterocolitis—multisystem organ failure of the newborn?*, Acta Paedr, 1994, Supp 396, p. 21-3.
Murch, SH, *Toll of allergy reduced by probiotics*, The Lancet, 2001; 357: 1057-1059.
Nagakura, T et al., *Dietary supplementation with fish oil rich in omega-3 polyunsaturated fatty acids in children with bronchial asthma*, European Respiratory Journal, vol. 16, No. 5, Nov. 2000, pp. 861-865.
Nelson, KB et al., *Neonatal Cytokines and Coagulation Factors in Children with Cerebral Palsy*, Ann Neurol, 1998; 44(4): pp. 665-675.
Ouwehand, AC et al., *The mucus binding of Bifidobacterium lactic Bb12 is enhanced in the presence of Lactobacillus GG and Lact delbrueckii subsp bulgaricus*, The Society for Applied Microbiology—Letters in Applied Microbiology, 2000, vol. 30, pp. 10-13.
Pena, Jeremy Andrew et al., *Lactobacillus rhamnosus GG decreases TNF-a production in lipopolysaccharide-activated murine macrophages by a contact-independent mechanism*, Cellular Microbiology, Blackwell Science, vol. 5, No. 4, Apr. 2003, pp. 277-285.
Bourlioux, Pierre et al., *The intestine and its microflora are partners for the protection of the host: report on the Danone Symposium "The Intelligent Intestine," held in Paris, Jun. 14, 2002*[1,2], American Journal of Clinical Nutrition, Oct. 2003, vol. 78, No. 4, pp. 675-783. [Online] http://www.ajcn.org/cgi/content/full/78/4/675.
Remick, D, *Lung and gut injury induced by tumour necrosis factor*, Res Immunol, 1993; 144: p. 326-331.
Stuyt, Rogier JL et al., *Differential Roles of Interleukin-18 (IL-18) and IL-12 for Induction of Gamma Interferon by Staphylococcal Cell Wall Components and Superantigens*, Infection and Immunity, Aug. 2001, vol. 69, No. 8, pp. 5025-5030.
Rubaltelli, Firmino F et al., *Probiotics Feeding Prevents Necrotizing Enterocolitis in Preterm Infants: A Prospective Double-Blind Study*, Pediatric Research, vol. 47, No. 4, Part 2, Apr. 2000, p. 346A.
Saavedra, J et al., *Long-term consumption of infant formulas containing live probiotic bacteria: tolerance and safety*[1-3], American Journal of Clinical Nutrition, 2004, vol. 79, pp. 261-267.
Saavedra, J, *Clinical applications of probiotic agents*[1-3], American Journal of Clinical Nutrition, 2001, vol. 73(Suppl), pp. 1147-1151.
Salminen, S et al., *Probiotics Demonstrating Efficacy in Clinical Settings*, Editorial Commentary—CID, 2001, vol. 32, pp. 1577-1578.
Sansonetti, PJ et al., *Interleukin-8 Controls Bacterial Transepithelial Translocation at the Cost of Epithelial Destruction in Experimental Shigellosis*, Infect Immun, 1999; 67(3): p. 1471-1480.
Schrezenmeir, Jurgen et al., *Probiotics, prebiotics, and synbiotics—approaching a definition*[1,2,3], American Journal of Clinical Nutrition, Feb. 2001, vol. 73, No. 2, pp. 361S-364S. [Online] http://www.ajcn.org/cgi/content/full/73/2/361S.
Sherman, Michael P et al., *Neonatal small bowel epithelia: enhancing anti-bacterial defense with lactoferrin and Lactobacillus GG*, Biometals, vol. 17, No. 3, Jun. 2004, pp. 285-289.

Sugawara, Shunji et al., *Lipoteichoic Acid Acts as an Antagonist and an Agonist of Lipopolysaccharide on Human Gingival Fibroblasts and Monocytes in a CD14-Dependent Manner*, Infection and Immunity, Apr. 1999, vol. 67, No. 4, pp. 1623-1632. [Online] http://iai.asm.org/cgi/content/full/67/4/1623.
Silen, ML et al., *Cachectin/Tumor Necrosis Factor Production by Fetal and Newborn Rat Hepatic Macrophages*, J Pediatr Surg, 1989; 24(1), p. 34-38.
Stratakis, CA et al., *Interleukin-6 elevation in critically ill infants with sepsis and necrotizing enterocolitis*, The Journal of Pediatrics, 1994; 125(3), p. 504. [Online] http://www2.us.elsevierhealth.com.
Tejada-Simon, MV et al., *Ingestion of Yogurt Containing Lactobacillus acidophilus and Bifidobacterium to Potentiate Immunoglobulin A Responses to Cholera Toxin in Mice*, Journal of Dairy Science, 1999, vol. 82, pp. 649-660.
Van Der Poll, T et al., *Release of Soluble Receptors for Tumor Necrosis Factor in Clinical Sepsis and Experimental Endotoxemia*, J Infect Dis, 1993, 168: p. 955-960.
Vidal, Karine et al., *Lipoteichoic Acids from Lactobacillus johnsonii Strain La1 and Lactobacillus acidophilus Strain La10 Antagonize the Responsiveness of Human Intestinal Epithelial HT29 Cells to Lipopolysaccharide and Gram-Negative Bacteria*, Infection and Immunity, Apr. 2002, vol. 70, No. 4, p. 2057-2064. [Online] http://iai.asm.org/cgi/content/full/70/4/2057.
Walker, WA, *Development of the Intestinal Mucosal Barrier*, J Pediatr Gastroenterol Nutr, 2002; 34 (Suppl 1): p. 33-39.
Wang, JE et al., *Peptidoglycan and Lipoteichoic Acid from Staphylococcus aureus Induce Tumor Necrosis Factor Alpha, Interleukin 6 (IL-6), and IL-10 Production in Both T Cells and Monocytes in a Human Whole Blood Model*, infection and Immunity, Jul. 2000, vol. 68, No. 7, pp. 3965-3970. [Online] http://iai.asm.org/cgi/content/full/68/7/3965.
Wanke, CA, *Do probiotics prevent childhood illnesses?*, BMJ, 2001, vol. 322, pp. 1318-1319.
Written Opinion of the International Searching Authority for application No. PCT/US2006/010415, International filing date Mar. 22, 2006. Date of mailing Aug. 14, 2006.
Written Opinion of the International Searching Authority for application No. PCT/US2006/010321, International filing date Mar. 22, 2006. Date of mailing Aug. 14, 2006.
Xu, Jian et al., *Honor thy symbionts*, PNAS, Sep. 2, 2003, vol. 100, No. 18, pp. 10452-10459. [Online] http://www.pnas.org/cgi/content/full/100/18/10452.
Yamasaki, Y et al., *Involvement of Cytokine Production in Pathogenesis of Transient Cerebral Ischemic Damage*, Keio J Med, 1996; 45(3): p. 225-9.
Yasui, H et al., *Detection of Bifidobacterium Strains that Induce large Quantities of IgA*, Microbial Ecology in Health and Disease, 1992, vol. 5, pp. 155-162.
Yasui, Hisako et al., *Protection against Influenza Virus Infection of Mice Fed Bifidobacterium breve YIT4064*, Clinical and Diagnostic Laboratory Immunology, American Society for Microbiology, US, vol. 6, No. 2, Mar. 1999, pp. 186-192.
Isolauri, E et al., *Lactobacillus casei Strain GG Reverses Increased Intestinal Permeability Induced by Cow Milk in Suckling Rats*, Gastroenterology 1993; 105: 1643-1650.

\* cited by examiner

Figure 3

| | Lactobacillus rhamnosus | Enterococcus | E.coli | Staphylococcus aureus | Bacteroides |
|---|---|---|---|---|---|
| PBS | - | + | + | +- | ++ |
| LGG | +++ | ++ | ++ | - | +++ |

Info: We can detect LGG (bacterial cultures, not PCR) in faeces of the mother mice two days after feeding with LGG

METHOD FOR PREVENTING OR TREATING THE DEVELOPMENT OF RESPIRATORY ALLERGIES

CROSS-REFERENCE TO RELATED PATENTS AND PATENT APPLICATIONS

This application is a divisional application and claims the priority benefit of U.S. patent application Ser. No. 11/144,287 filed Jun. 3, 2005, which is a continuation application of U.S. patent application Ser. No. 11/106,792 filed Apr. 15, 2005, now abandoned and which are incorporated by reference herein in their entirety.

BACKGROUND OF THE INVENTION (1) Field of the Invention

The present invention relates generally to a method for preventing or treating the development of respiratory allergies.

(2) Description of the Related Art

Allergy is defined as an "abnormal hypersensitivity to a substance which is normally tolerated and generally considered harmless." The symptoms of allergies can range from a runny nose to anaphylactic shock. Nearly 50 million Americans suffer from allergic disease, and the incidence of these illnesses is increasing.

There are two basic phases involved with the allergic response. The first stage involves the development of the early phase of an immediate-type hypersensitivity response to allergens. The first time an allergen meets the immune system, no allergic reaction occurs. Instead, the immune system prepares itself for future encounters with the allergen. Macrophages, which are scavenger cells, surround and break up the invading allergen. The macrophages then display the allergen fragments on their cell walls to T lymphocytes, which are the main orchestraters of the body's immune reaction.

This cognitive signal plus several non-cognitive signals (e.g. cytokines) activate the naïve T-cells and instruct the T-cell differentiation into T-cell effector subpopulations. The key players in the allergic cascade are T-cells of the Th-2 phenotype (TH-2). TH-2 type T-cells are characterized by the secretion of several cytokines including interleukin-4 (IL-4), IL-5 and IL-13. The cytokines IL-4 and IL-13 then activate B lymphocytes which produce antibodies of the subclass E (IgE). IgE antibodies are directed against the particular allergen. The interaction of specific IgE antibodies on the surface of effector cells (mast cells and basophils) with an allergen triggers the early phase of immediate type hypersensitivity responses.

This mast cell activation usually occurs within minutes after the second exposure to an allergen. IgE antibodies on mast cells, constructed during the sensitization phase, recognize the allergen and bind to the invader. Once the allergen is bound to the receptor, granules in the mast cells release their contents. These contents, or mediators, are proinflammatory substances such as histamine, platelet-activating factor, prostaglandins, cytokines and leukotrienes. These mediators actually trigger the allergy attack. Histamine stimulates mucus production and causes redness, swelling, and inflammation. Prostaglandins constrict airways and enlarge blood vessels.

The second phase of the allergic immune response is characterized by infiltration of inflammatory cells, such as eosinophils, into the airways after an allergen exposure. An important linkage between sensitization and inflammation is represented by T-cells that secrete mediators not only involved in IgE synthesis, but also responsible for eosinophil recruitment, activation and survival. The tissue mast cells and neighboring cells produce chemical messengers that signal circulating basophils, eosinophils, and other cells to migrate into that tissue and help fight the foreign material. Eosinophils secrete chemicals of their own that sustain inflammation, cause tissue damage, and recruit yet more immune cells. This phase can occur anywhere between several hours and several days after the allergen exposure and can last for hours and even days.

Respiratory allergy is a particular type of allergy that affects the respiratory tract. The lining of the airway from the nose to the lungs is similar in structure and is often similarly affected by the allergic process. Therefore, an allergen that affects the nose or sinus also could affect the lungs.

For example, allergic rhinitis, also known as hay fever, is caused by allergic reactions of the mucous membranes in the nose and airway to allergens in the air. Symptoms of allergic rhinitis often include itchy nose, throat and eyes and excessive sneezing. Stuffy or runny nose often follow.

As allergens in one area of the respiratory tract can affect other areas of the respiratory tract, rhinitis in the nasal passages can lead to asthma, which is a much more serious illness that occurs in the lungs. Asthma is characterized by development of airway hyperreactivity, breathlessness, wheezing on exhale, dry cough and a feeling of tightness in the chest. Repeated allergen exposure can sustain the inflammatory immune response in the airways, resulting in a remodeling of the airways, commonly known as chronic asthma. Not everyone with allergic rhinits will develop asthma symptoms, but a significant number, especially those with recurring, untreated allergies, will show lung inflammation changes. About forty percent of people with allergic rhinitis will actually develop full-blown asthma.

If the nasal inflammation that accompanies allergic rhinitis reaches the sinuses, the result can be an uncomfortable infection called sinusitis, or rhino-sinusitis, in which the sinuses cannot empty themselves of bacteria. Symptoms include nasal congestion, runny nose, sore throat, fever, headache, fatigue and cough, as well as pain in the forehead, behind the cheeks, and even aching teeth and jaw.

Respiratory allergies are one of the most common afflictions of childhood. As with adults, respiratory allergies in children are most likely to appear in the form of allergic rhinitis and asthma.

The prevention of respiratory allergies is especially important in infants and young children, as it appears that early allergic sensitization to allergens is associated with a delay in the maturation of normal immune responses. Additionally, allergic sensitization is generally considered the first step in developing atopic disease. Baena-Cagnani, *Role of Food Allergy in Asthma in Childhood*, Allergy. Clin. Immun. 1(2): 145-149 (2001). Frequently, asthma that begins early in life is associated with atopy, thus early allergic sensitization seems to play an important role in persistent asthma as well. Martinez, F., *Development of Wheezing Disorders and Asthma in Preschool Children*, Pediatr. 109:362-367 (2002).

Not only is there a strong association between allergic sensitization and asthma, but the association appears to be age-dependent. Although few children become allergen sensitized during the first few years of life, the great majority of those who do become sensitized during this period develop asthma-like symptoms later in life. Martinez, F. *Viruses and Atopic Sensitization in the First Years of Life*, Am. J. Respir. Crit. Care Med., 162:S95-S99 (2000). Thus, it is important to find ways to prevent early allergen sensitization and prevent respiratory allergies later in life.

There is increasing evidence that many aspects of health and disease are determined not only during infancy, but also during pregnancy. This is especially true with allergic disease, where immune responses at birth implicate intrauterine exposure as a primary sensitization event. For example, allergen-specific T-cells are already present at birth and early sensitization to food allergens are identified as predictors for later development of respiratory allergies. Illi, et al., *The Natural Course of Atopic Dermatitis from Birth to Age 7 Years and the Association with Asthma*, Clin. Exp. Allergy 27:28-35 (1997). In addition, lung development begins very early after fertilization and continues for at least two or three years after birth. Thus, both prenatal and postnatal airway development are important in the pathogenesis of respiratory allergy in infants and children.

It has also been shown that the human fetus develops IgE-producing B cells early in gestation and is capable of producing IgE antibodies in response to appropriate antigenic stimuli in a manner analogous to the well-recognized IgM responses that are observed in various prenatal infections. Weil, G., et al., *Prenatal Allergic Sensitization to Helminth Antigens in Offspring of Parasite-Infected Mothers*, J. Clin. Invest. 71:1124-1129 (1983). This also illustrates the importance of preventing both prenatal and postnatal allergic sensitization to respiratory allergens.

Traditional medications for respiratory allergies include antihistamines, topical nasal steroids, decongestants, and cromolyn solution. As an alternative to traditional medications, probiotics have emerged as possible treatments for certain types of allergies.

Probiotic bacteria are living microorganisms that exert beneficial effects on the health of the host. *Lactobacillus* spp. and *Bifidobacterium* spp., which are normal inhabitants of the healthy intestine, are common species of probiotics. Unfortunately, there are very few published studies on the clinical effects of probiotic supplementation in infants. Agostoni, C., et al, *Probiotic Bacteria in Dietetic Products for Infants: A Commentary by the ESPGHAN Committee on Nutrition*, J. Pediatr. Gastro. Nutr. 38:365-74 (2004).

U.S. Patent App. No. 20040208863 to Versalovic, et al. is directed to a compound which has anti-inflammatory activity and is secreted from lactic acid bacteria. The application describes the use of *Lactobacillus* GG (LGG) to inhibit pro-inflammatory cytokine production. The reference however, focuses on adult models and does not disclose or suggest that the administration of LGG during pregnancy or infancy would be beneficial.

U.S. Pat. No. 6,506,380 to Isolauri, et al., describes a method of suppressing food-induced hypersensitivity reactions in patients suffering from food allergy by administering to them a probiotic. The reference does not, however, disclose the use of probiotics to treat respiratory allergies. Additionally, although the patent does discuss the treatment of infants with probiotics, it does not disclose the importance of treating both pre- and postnatally.

Several studies have focused on the pre- and postnatal administration of probiotics to prevent certain allergies in infants and children. For example, one study concludes that probiotics, administered during pregnancy and breast-feeding, might confer protection from atopic eczema for the infant. Rautava, S, et al., *Probiotics During Pregnancy and Breast-Feeding Might Confer Immunomodulatory Protection Against Atopic Disease in the Infant*, J. Allergy Clin. Immunol. 109:119-121 (2002). While the study found that fewer infants in the probiotic group developed atopic eczema than did the placebo group, the study concluded that the administration of probiotics had "no effect on the traditional objective correlates of atopy and atopic disease (i.e., skin prick test results and serum IgE antibodies)." Thus, because the traditional markers of atopy were unaffected by the probiotic supplementation, it must be assumed that the probiotic administration was effective only for atopic eczema and not for all allergies.

Similarly, a 2001 study concluded that probiotics can prevent atopic eczema, but that "concentration of total IgE and frequencies of increased antigen-specific IgE concentrations and of positive reactions in skin-prick tests were very similar between probiotic and placebo groups." Kalliomaki, M., *Probiotics in Primary Prevention of Atopic Disease: a Randomized Placebo-Controlled Trial*, Lancet 357:1076-79 (2001). Again, these results suggest that the probiotic administration, while effective for atopic eczema, would not necessarily be effective for other types of allergies.

SUMMARY OF THE INVENTION

Briefly, the present invention is directed to novel method for preventing or treating the development of respiratory allergies in a subject, the method comprising prenatally administering and/or postnatally administering to the subject a therapeutically effective amount of LGG.

The present invention is also directed to a novel method for preventing or treating allergy-induced inflammation in the lung and airways of a subject, the method comprising prenatally administering and/or postnatally administering to the subject a therapeutically effective amount of LGG.

In another aspect the present invention is directed to a novel method for preventing or treating the release of one or more pro-inflammatory cytokines in a subject, the method comprising prenatally administering and/or postnatally administering to the subject a therapeutically effective amount of LGG.

Additionally, the present invention is directed to a novel method for preventing or treating the production of serum IgE antibodies in a subject, the method comprising prenatally administering and/or postnatally administering to the subject a therapeutically effective amount of LGG.

The present invention is also directed to a novel method for increasing the production of serum IgA antibodies in a subject, the method comprising prenatally administering and/or postnatally administering to the subject a therapeutically effective amount of LGG.

Among the several advantages found to be achieved by the present invention, is that it provides a method for preventing or treating respiratory allergies in subjects without the necessity of administering medications. Further, the subject is benefited by the reduction or prevention of allergy-induced inflammation of the lung or airways, including a reduction in airway tissue inflammation and airway lumen inflammation. The invention also provides a decrease in mucus production and a widening of the airways. The invention also provides a reduction or prevention in the release of pro-inflammatory cytokines and serum IgE antibodies as well as an increase in the production of serum IgA. These benefits were surprising and unexpected, as similar studies provided contrary results.

BRIEF DESCRIPTION OF THE DRAWINGS

For a more complete understanding of the present invention, reference is now made to the following descriptions taken in conjunction with the accompanying drawings.

FIG. 3 illustrates the bacteria in the feces of LGG-treated mice versus control.

DETAILED DESCRIPTION OF THE PREFERRED EMBODIMENTS

Figure 1:
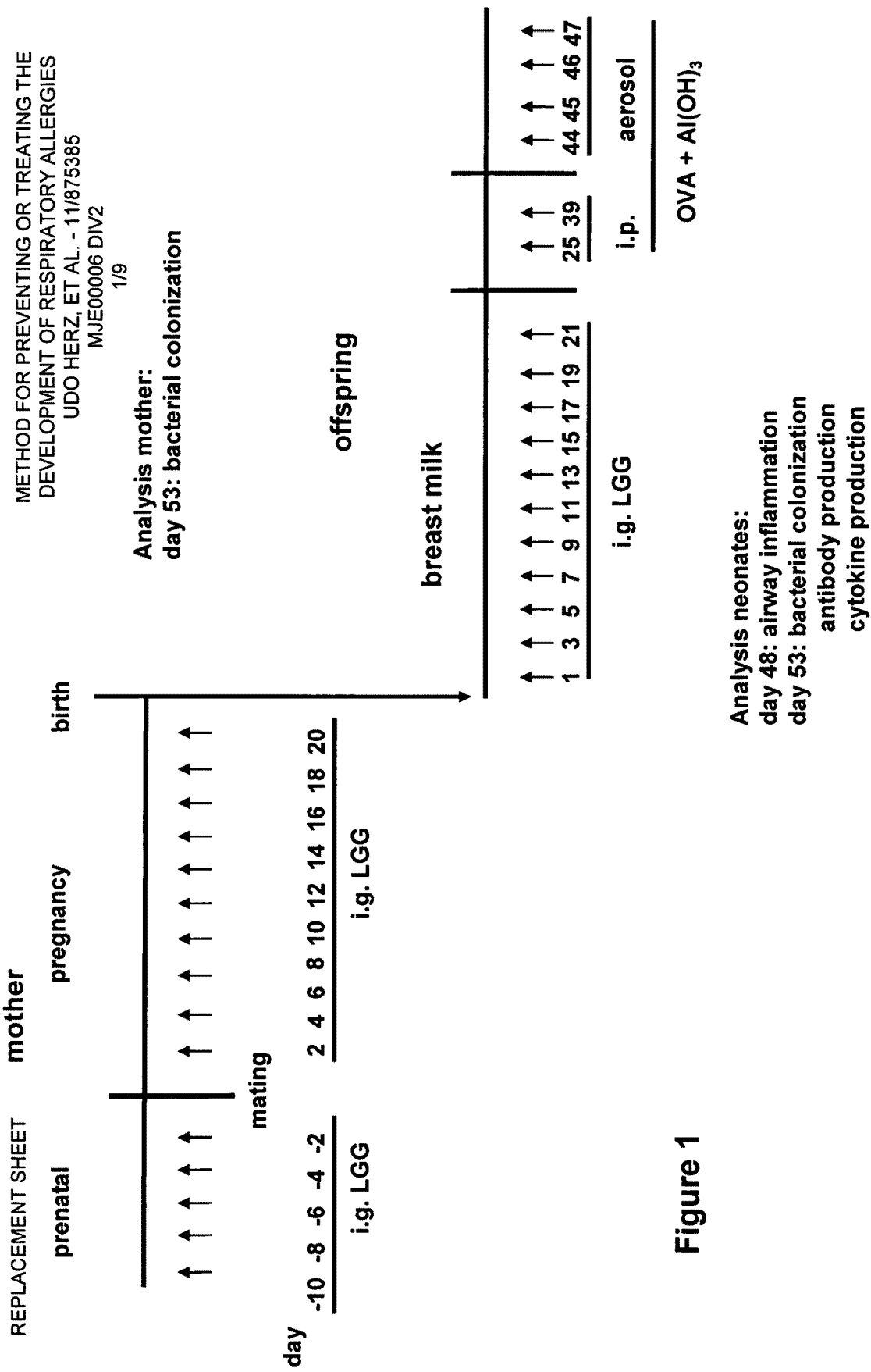
FIG. 1 illustrates the protocol utilized during the present invention.

Reference now will be made in detail to the embodiments of the invention, one or more examples of which are set forth below. Each example is provided by way of explanation of the invention, not a limitation of the invention. In fact, it will be apparent to those skilled in the art that various modifications and variations can be made in the present invention without departing from the scope or spirit of the invention. For instance, features illustrated or described as part of one embodiment, can be used on another embodiment to yield a still further embodiment.

Thus, it is intended that the present invention covers such modifications and variations as come within the scope of the appended claims and their equivalents. Other objects, features and aspects of the present invention are disclosed in or are obvious from the following detailed description. It is to be understood by one of ordinary skill in the art that the present discussion is a description of exemplary embodiments only, and is not intended as limiting the broader aspects of the present invention.

Definitions

The term "probiotic" means a microorganism that exerts beneficial effects on the health of the host.

The term "prebiotic", as used herein, means a non-digestible food ingredient that stimulates the growth and/or activity of probiotics.

The term "subject" means any mammal, preferably a human.

As used herein, the term "treating" means ameliorating, improving or remedying a disease, disorder, or symptom of a disease or condition.

The term "preventing" means to stop or hinder a disease, disorder, or symptom of a disease or condition through some action.

The terms "therapeutically effective amount" refer to an amount that results in an improvement or remediation of the disease, disorder, or symptoms of the disease or condition.

The terms "prenatal administration" or "prenatally administering" mean any administration to the pregnant mother of an unborn subject.

The terms "postnatal administration" or "postnatally administering" mean any administration to a subject from the time of birth until about 1 year of life.

As used herein, the term "infant formula" means a composition that satisfies the nutrient requirements of an infant by being a substitute for human milk. In the United States, the contents of an infant formula are dictated by the federal regulations set forth at 21 C.F.R. Sections 100, 106, and 107. These regulations define macronutrient, vitamin, mineral, and other ingredient levels in an effort to stimulate the nutritional and other properties of human breast milk.

Invention

In accordance with the present invention, a novel method for preventing or treating the development of respiratory allergies in a subject has been discovered. The method comprises prenatally administering and/or postnatally administering a therapeutically effective amount of LGG to the subject. According to the invention, the prenatal and/or postnatal administration of LGG to a subject while unborn and during infancy can prevent or treat the development of respiratory allergies later in life.

LGG is a probiotic strain isolated from healthy human intestinal flora. It was disclosed in U.S. Pat. No. 5,032,399 to Gorbach, et al, which is herein incorporated in its entirety, by reference thereto. LGG is resistant to most antibiotics, stable in the presence of acid and bile, and attaches avidly to mucosal cells of the human intestinal tract. It survives for 1-3 days in most individuals and up to 7 days in 30% of subjects. In addition to its colonization ability, LGG also beneficially affects mucosal immune responses. LGG is deposited with the depository authority American Type Culture Collection under accession number ATCC 53103.

In the method of the invention, a therapeutically effective amount of LGG may correspond to between about $1 \times 10^4$ and $1 \times 10^{12}$ cfu/L/kg/day. In another embodiment, the present invention comprises the administration of between about $1 \times 10^6$ and $1 \times 10^9$ cfu/L/kg/day LGG. In yet another embodiment, the present invention comprises the administration of about $1 \times 10^8$ cfu/L/kg/day LGG.

The form of administration of LGG in the method of the invention is not critical, as long as a therapeutically effective amount is administered. For prenatal administration, the LGG can be administered to the pregnant mother of the unborn subject and can thereby be imparted to the unborn subject. The prenatal administration can be administered to the mother in the form of a supplement. For example, the LGG can be ingested in the form of a pill, tablet, capsule, caplet, powder, liquid or gel. In this embodiment of the method, an LGG supplement can be ingested in combination with other nutrient supplements, such as vitamins.

In another embodiment, the prenatally administered LGG can be encapsulated in a sugar, fat, or polysaccharide matrix to further increase the probability of bacterial survival. Compositions of the present invention can also be provided in a form suitable for consumption selected from the group consisting of beverage, milk, yogurt, fruit juice, fruit-based drink, chewable tablet, cookie, cracker, or a combination thereof.

If, during the first year of life, the subject is breast-fed, the postnatal administration of LGG can be via the mother's breast milk. In this embodiment, the mother can continue LGG supplementation during the time period that she breastfeeds, thereby transferring an effective amount of LGG to her baby via breast milk.

It during the first year of life, the subject is formula-fed, or if the mother supplements breast-feeding with formula-feeding, the LGG can be supplemented into infant formula which is then fed to the subject. This, too, is a method for postnatal administration of the LGG.

In an embodiment, the infant formula for use in the present invention is nutritionally complete and contains suitable types and amounts of lipid, carbohydrate, protein, vitamins and minerals. The amount of lipid or fat typically can vary from about 3 to about 7 g/100 kcal. The amount of protein typically can vary from about 1 to about 5 g/100 kcal. The amount of carbohydrate typically can vary from about 8 to about 12 g/100 kcal. Protein sources can be any used in the art, e.g., nonfat milk, whey protein, casein, soy protein, hydrolyzed protein, amino acids, and the like. Carbohydrate sources can be any used in the art, e.g., lactose, glucose, corn syrup solids, maltodextrins, sucrose, starch, rice syrup solids, and the like. Lipid sources can be any used in the art, e.g., vegetable oils such as palm oil, soybean oil, palmolein, coconut oil, medium chain triglyceride oil, high oleic sunflower oil, high oleic safflower oil, and the like.

Conveniently, commercially available infant formula can be used. For example, Enfamil®, Enfamil® Premature Formula, Enfamil® with Iron, Lactofree®, Nutramigen®, Pregestimil®, and ProSobee® (available from Mead Johnson & Company, Evansville, Ind., U.S.A.) may be supplemented with suitable levels of LGG and used in practice of the method of the invention.

As an alternative to an infant formula, the postnatally administered LGG can be administered as a supplement not integral to the formula feeding. For example, LGG can be ingested in the form of a pill, tablet, capsule, caplet, powder, liquid or gel. In this embodiment of the method, an LGG supplement can be ingested in combination with other nutrient supplements, such as vitamins.

In another embodiment, the LGG is encapsulated in a sugar, fat, or polysaccharide matrix to further increase the probability of bacterial survival. Compositions of the present invention can also be provided in a form suitable for infants selected from the group consisting of follow-on formula, beverage, milk, yogurt, fruit juice, fruit-based drink, chewable tablet, cookie, cracker, or a combination thereof.

In an embodiment of the method of the invention, the postnatal administration of LGG continues for at least 3 months. In another embodiment of the invention, the postnatal administration of LGG continues for at least 6 months. In yet another embodiment of the invention, the postnatal administration of LGG continues for at least 12 months. In a particular embodiment of the invention, the postnatal administration of LGG continues indefinitely.

In one embodiment of the invention, the prenatally or postnatally administered LGG can be combined with one or more additional probiotics. Any probiotic known in the art will be acceptable in this embodiment. In a particular embodiment, the probiotic is chosen from the group consisting of Lactobacillus and Bifidobacterium.

In another embodiment of the invention, the prenatally or postnatally administered LGG can be combined with one or more prebiotics. Any prebiotic known in the art will be acceptable in this embodiment. Prebiotics of the present invention may include lactulose, galacto-oligosaccharide, fructo-oligosaccharide, isomalto-oligosaccharide, soybean oligosaccharides, lactosucrose, xylo-oligosacchairde, and gentio-oligosaccharides.

In a method of the present invention, the prenatal and/or postnatal administration of LGG prevents or treats the development of allergic rhinitis, asthma or sinusitis.

In another method of the present invention, the prenatal and/or postnatal administration of LGG prevents or treats allergy-induced inflammation in the lung and airways of a subject. Specifically, the method of the invention can prevent or treat airway tissue inflammation, airway lumen inflammation, decrease mucus production, or widen the airway.

In yet another method of the present invention, the prenatal and/or postnatal administration of LGG reduces or prevents the release of one or more pro-inflammatory cytokines. As used herein, "pro-inflammatory" cytokines include those known in the art to be involved in the up-regulation of inflammatory reactions. Examples include, but are not limited to IFN-γ, MCP-1, IL-6 and IL-10.

In a particular embodiment of the invention, the prenatal and/or postnatal administration of LGG prevents or reduces the production of serum IgE antibodies in subjects. In another embodiment, the prenatal and/or postnatal administration of LGG increases the production of serum IgA antibodies in subjects.

The following examples describe various embodiments of the present invention. Other embodiments within the scope of the claims herein will be apparent to one skilled in the art from consideration of the specification or practice of the invention as disclosed herein. It is intended that the specification, together with the examples, be considered to be exemplary only, with the scope and spirit of the invention being indicated by the claims which follow the examples. In the examples, all percentages are given on a weight basis unless otherwise indicated.

EXAMPLE 1

This example describes the materials and methods necessary to show the effect of the prenatal administration of LGG on the development of respiratory allergies and inflammation in the lung and airways. Female bag albino, substrain c (BALB/c) mice aged 6-8 weeks were obtained from Harlaan Hinkelmann (Hannover, Germany). They were maintained on an Ovalbumin (OVA)-free diet. All of the experimental procedures were approved by the animal ethics committee.

Prenatal *Lactobacillus Rhamnosus* GG (LGG)-Exposure

Female BALB/c mice received 5 intragastric (i.g.) applications of $10^8$ colony forming units (cfu) freeze-dried LGG in a volume of 200 µl (reconstituted in phosphate-buffered saline (PBS)) on days −10, −8, −6, −4 and −2 prior to mating. After mating and during the gestation and lactation period, mice of all groups were treated intragastrically with $10^8$ cfu freeze-dried LGG in a volume of 200 µl every second day. Age matched, sham-exposed control animals received PBS instead of LGG (control group).

Neonatal OVA-Exposure

At the age of 25 days, and then again at the age of 39 days, the mice were sensitized to OVA by two intra-peritoneal (i.p.) injections of 10 µg OVA (grade VI; Sigma, Deisenhofen, Germany) emulsified in 1.5 mg Al(OH)$_3$ (Pierce, Rockford, USA) in a total volume of 200 µl.

To assess airway inflammation, the mice were placed in a Plexiglas chamber and exposed to aerosolized OVA (1% weight/volume diluted in PBS) for 20 minutes on days 44, 45, 46 and 47. Airway inflammation was assessed 24 hours after the last allergen-aerosol exposure.

Cytokine production and both IgE and IgA antibody response by OVA-sensitized mice was assessed on day 53.

Detection of LGG-DNA in Stool Samples

Stool samples (0.05 g) were weighed aseptically, placed into sterile tubes and homogenized in 1.4 ml lysis buffer. Genomic DNA extraction was performed according to the manufacturer's instruction (QIAamp DNA stool kit, Quiagen). DNA was amplified using the Hot-start PCR kit (Quiagen) with LGG-specific primer pairs (LGG sense: gagaagaatggtcggcagag and LGG antisense: catttcaccgctacacatgg).

Offspring: Exposure to OVA

At ages 25 and 39 days, offspring were sensitized to OVA by two i.p. injections of 10 μg OVA (grade VI; Sigma, Deisenhofen, Germany) emulsified in 1.5 mg Al(OH)$_3$ (Pierce, Rockford, USA) in a total volume of 200 μl. Antibody response of OVA sensitized mice was assessed on day 53.

At days 44, 45, 46 and 47 a subgroup of mice was placed in a Plexiglas chamber and exposed to aerosolized OVA (1% wt/vol diluted in PBS) for 20 minutes to assess airway inflammation.

Measurement of Serum Levels of Ova-Specific Antibodies

Levels of OVA-specific IgG1, IgG2a and IgE antibody titers were determined by ELISA technique at day 53. 96-well polystyrene flat-bottom microtiter plates (Greiner) were coated with OVA (20 μg/ml) diluted in 0.1 M carbonate coating buffer, pH 8.2 (for IgG1) or PBS (for IgE, IgG2a). Plates were incubated overnight at 4° C., washed three times with washing buffer (PBS/0.1% Tween 20) and blocked for 2 hours at room temperature using blocking solution (3% BSA/PBS). After washing the plates (3 times), samples (diluted in PBS/0.1% Tween 20) were added and incubated at 4° C. overnight followed by an incubation with biotin conjugated anti-mouse IgE, IgG2a or IgG1 monoclonal antibody (2.5 μg/ml, all antibodies from Pharmingen) for 2 hours at room temperature. The reaction was developed with streptavidin-peroxidase (diluted 1:1000) for 30 minutes at room temperature in the dark and tetramethylbenzidine (Roche) as substrate. The reaction was stopped with 2n-sulphuric acid and plates were measured at 450/490 nm.

Bronchioalveolar Lavage (BAL) and Cell Differentiation

Lavage fluids were collected 24 hours after the last OVA-aerosol exposure. Trachea was cannulated and BAL performed by two ravages with 0.8 ml ice-cold PBS. The recovered BAL-volume and the total cell number were determined. Cytospins were prepared for each sample by centrifugation of 50 μl BAL-fluid/150 μl PBS (100 g for 5 minutes). After fixation cytospins were stained with Diff Quick (Baxter Dade). Differential cell counts of 100 cells were performed. The cells were classified as neutrophils, eosinophils, macrophages or lymphocytes by standard morphological criteria.

EXAMPLE 2

Figure 2:
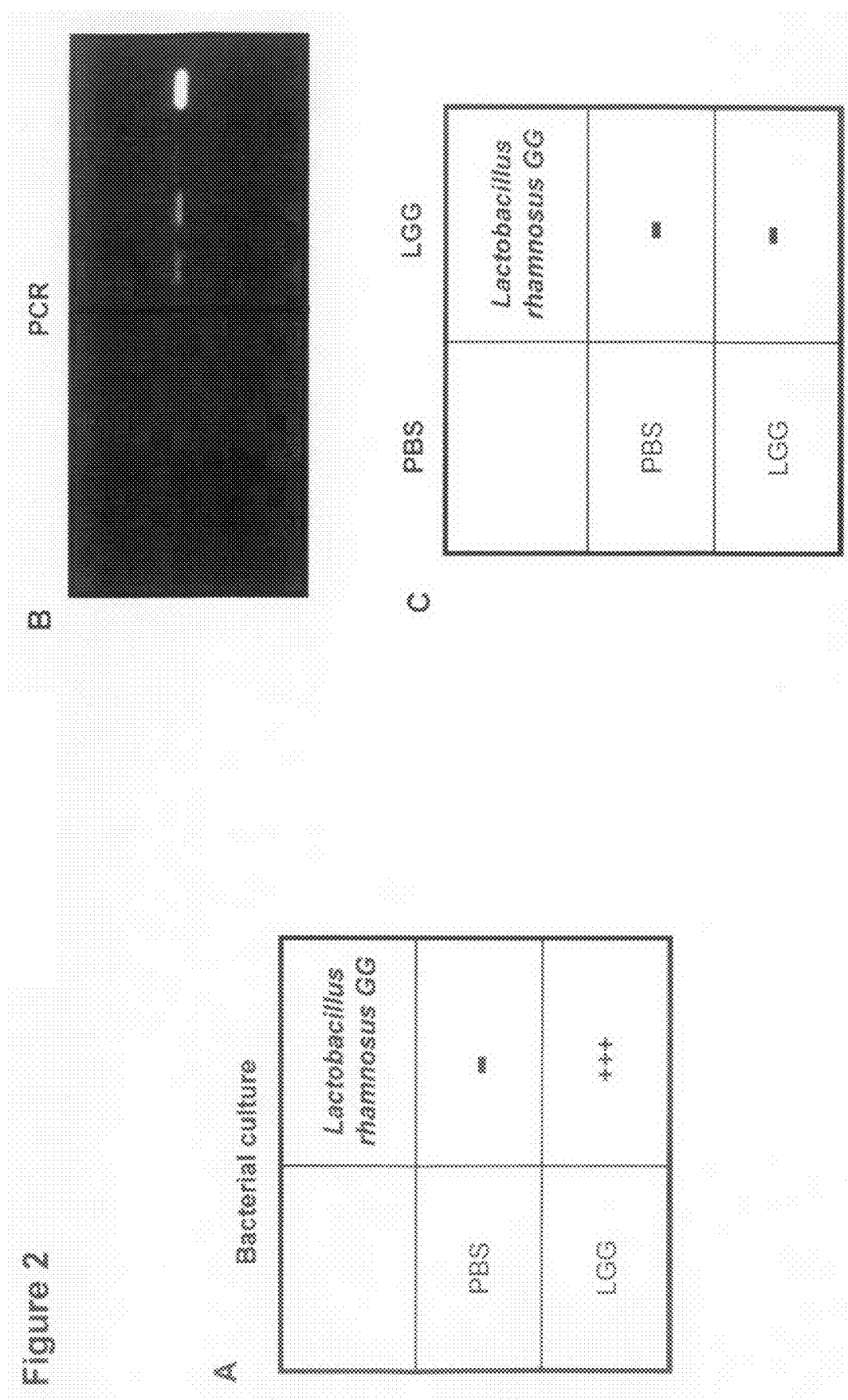
FIG. 2 illustrates the detection of LGG in the feces of LGG-treated mice (FIG. 2A) versus control (FIG. 2B) and whether maternal LGG treatment resulted in long-term LGG colonization (FIG. 2C).

This example illustrates the presence of LGG in the feces of the treated mice. The presence of LGG was assessed in fecal samples from LGG-treated mice versus mice which received PBS only. After microbial culturing, LGG was present in fecal samples from LGG treated mice whereas no LGG could be detected in PBS treated mice (FIG. 2A). To further confirm that the detected LGG is indeed identical with the LGG supplementation, DNA was prepared from fecal samples and amplified with LGG-PCR-specific primers. As shown in FIG. 1B, LGG specific PCR products could be detected in the samples from LGG treated mice whereas no LGG specific PCR products were detectable in samples from PBS treated mice (FIG. 2B). This result indicates that prenatal and early postnatal treatment of mice resulted in colonization of the gut and LGG is still detectable at least three weeks after the last LGG supplementation.

To assess whether maternal LGG treatment resulted in long-term (beyond 3 weeks after stopping the supplementation) LGG colonization in the mice, DNA was prepared from fecal samples from the mice at age of 53 days. The PCR analysis revealed that neither PBS treated nor LGG-treated mice were colonized with LOG (FIG. 2C). This result indicates that the maternal delivered LGG does not result in long term colonization of the offspring during the postnatal period To further assess whether the pre- and early postnatal LGG-supplementation impacts the distribution of the bacterial gut colonization, several bacterial strains (LGG Enterococcus, E. coli, Staphylococcus aureus, Bacteroides) were assessed in fecal samples. As shown in FIG. 3, there was a tendency that LGG-supplementation alters the bacterial colonization in a beneficial way. Bacteria of the species Enterococcus, E. coli, and Bacteroides were detected in higher numbers in fecal samples from LGG-supplemented mice compared to control mice (FIG. 3). In addition there was a tendency in of reduced Staphylococcus aureus colonization in the gut compared to PBS mice. These results indicate that LGG treatment improves the normal healthy gut colonization and in parallel, hinders the proliferation of (pathological) bacteria in mice guts.

EXAMPLE 3

Figure 4:
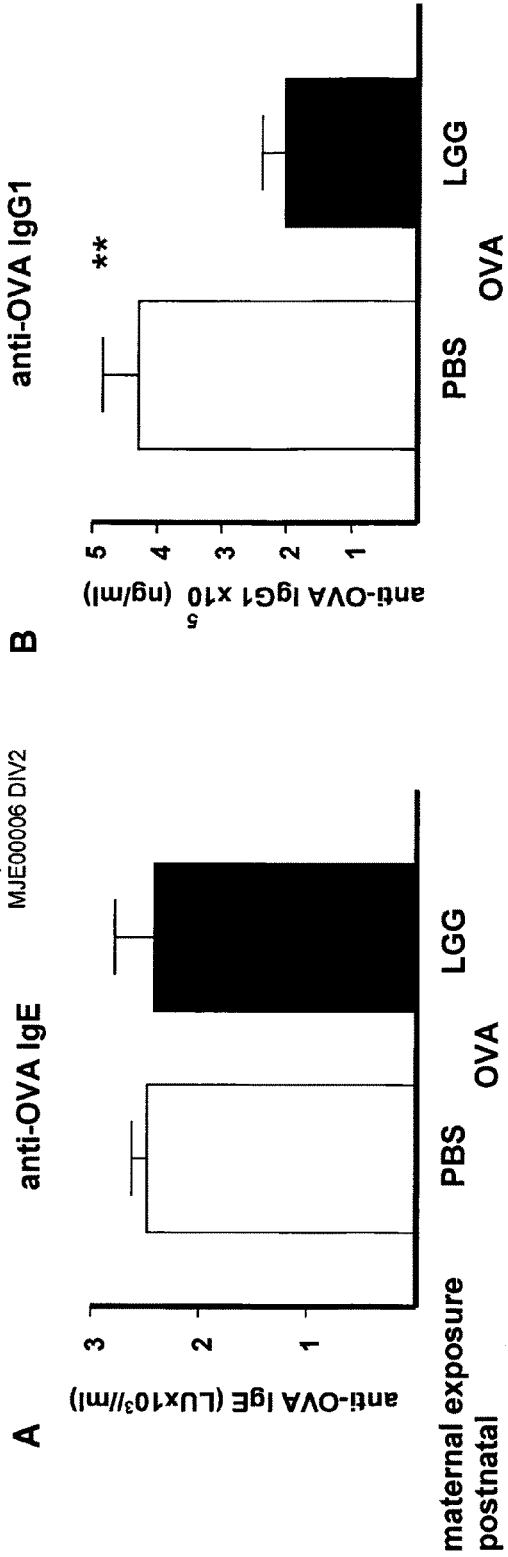
FIG. 4 illustrates the effect of LGG on serum anti-OVA-IgE (FIG. 4A), serum anti-OVA-IgG1 (FIG. 4B), and serum anti-OVA IgG2a (FIG. 4C).
Figure 4:
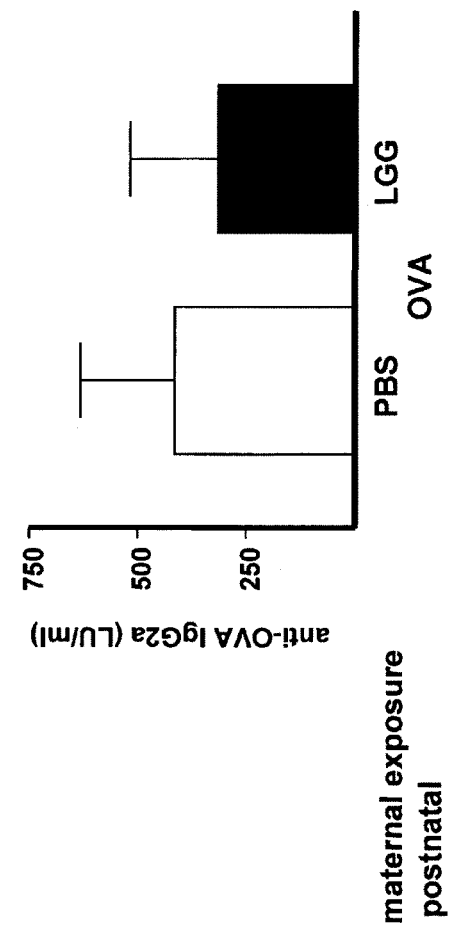

This example illustrates the effect of LGG on the production of serum allergen-specific antibodies in allergic subjects. It was further studied whether prenatal and early postnatal LGG-supplementation suppresses the development of an allergic phenotype later in life. Therefore, allergen-specific antibody production was assessed in the mice offspring after intra-peritonal sensitization to OVA following OVA-allergen aerosol exposure. As shown in FIGS. 4A and 4B, maternal LGG supplementation hinders the development of an allergen specific antibody response as indicated by a significant reduced production of anti-OVA IgG1 in prenatal and early postnatal exposed LGG mice compared to PBS controls (FIG. 4A, B). The murine IgG1 antibody subclass is the effector molecule in allergic manifestations such as positive skin prick tests and development of airway inflammation. Regarding this allergic effector function, the murine IgG1 antibody subclass equals the human IgE antibody subclass. Regarding the level of anti-OVA IgG2a antibody production, significant differences were detectable (FIG. 4C) These results indicate that maternal LGG-supplementation reduces allergic sensitization to a respiratory allergen later in life.

EXAMPLE 4

Figure 5:
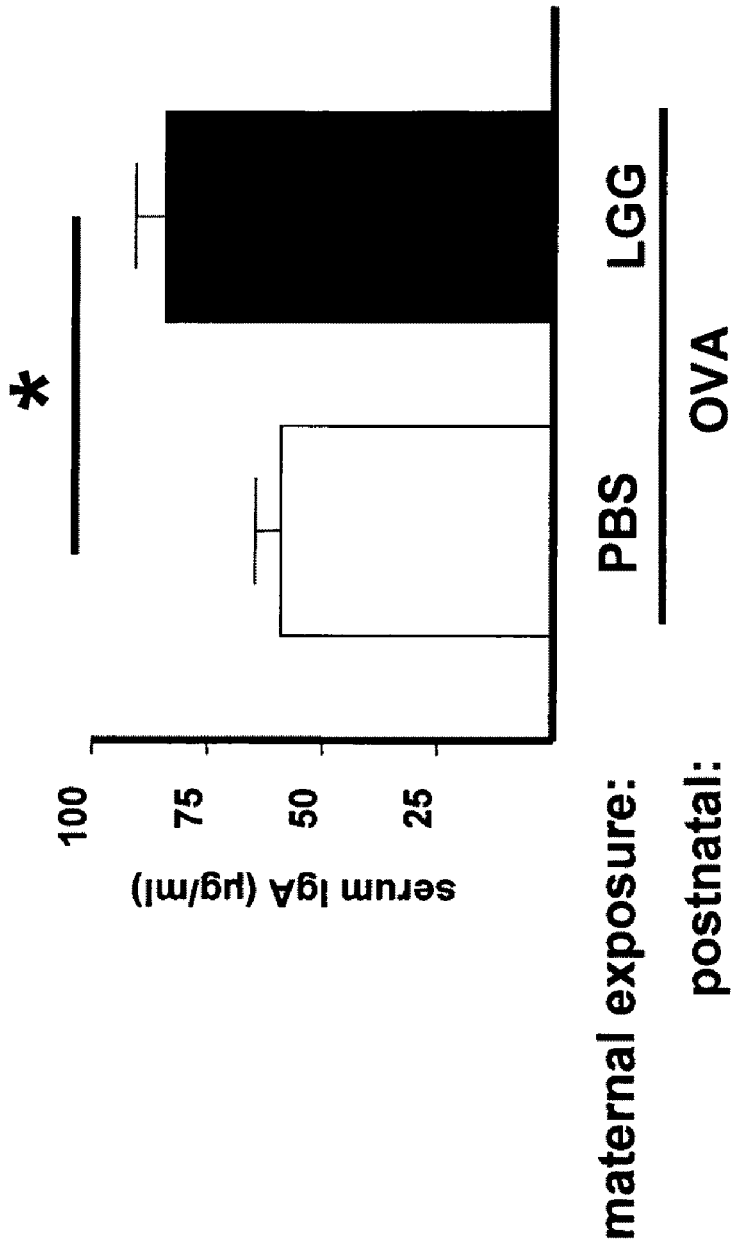
FIG. 5 illustrates the effect of LGG on the levels of serum IgA antibodies.

This example indicates the effect of LGG on the increase of serum IgA antibodies in subjects. Breast milk contains high levels of secretory antibodies of the subclass IgA. It is also well known that this antibody subclass is associated with the development of immunological tolerance after allergen exposure. Therefore, the result that there was a significant increase in serum IgA antibody production in offspring from LGG-supplemented mothers compared to offspring from control mothers (PBS) was surprising (FIG. 5). This result indicates that maternal LGG supplementation not only hinders the development of an allergic immune response in offspring, as indicated by a significantly decreased production of IgG1 antibodies, but also induces a pattern of antibody production (IgA) which is associated with the development of immunological tolerance.

EXAMPLE 5

Figure 6:
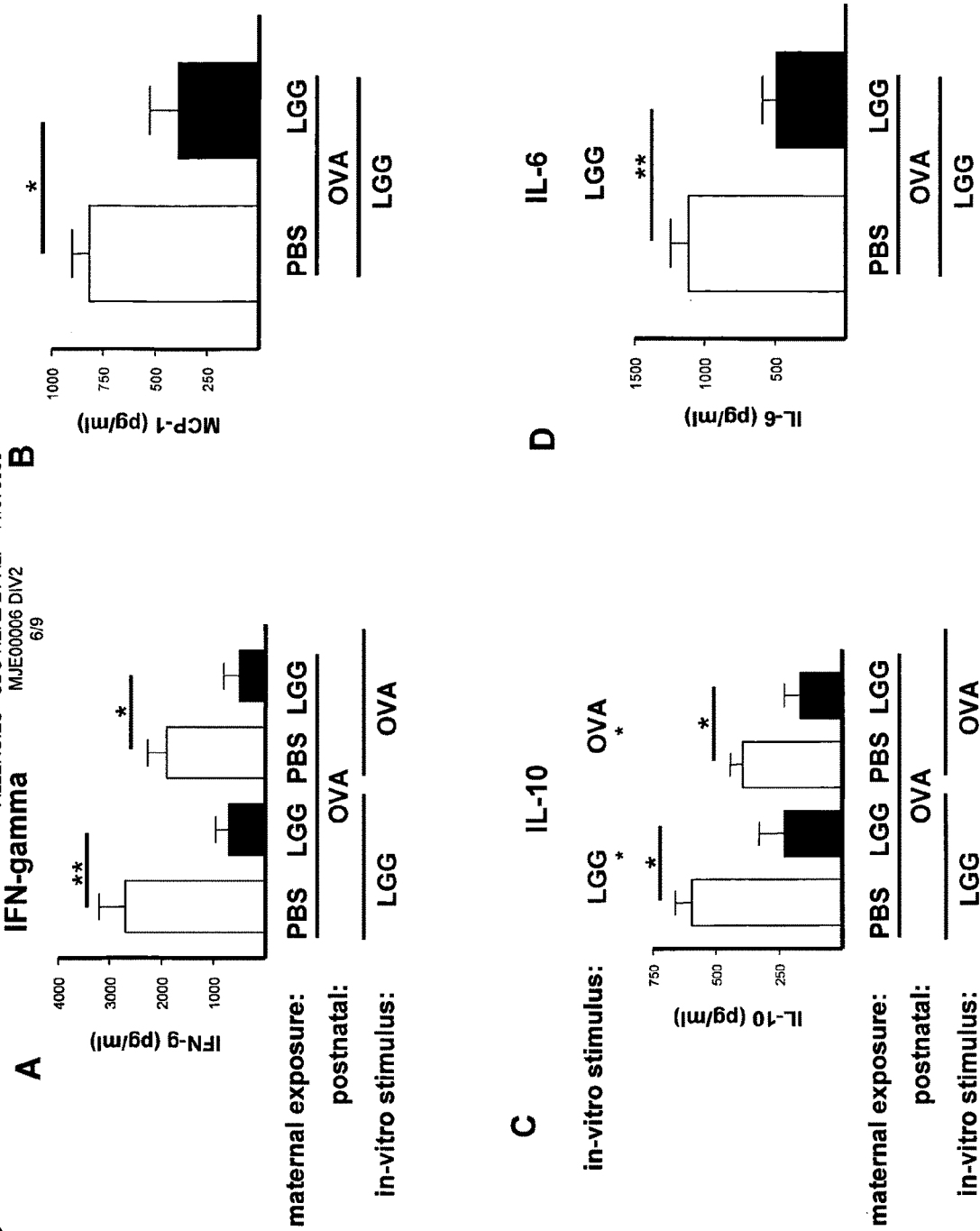
FIG. 6 illustrates the effect of LGG on various proinflammatory cytokines, IFN-y (FIG. 6A), MCP-I (FIG. 6B), IL-10 (FIG. 6C), and IL-6 (FIG. 6D) in OVA-sensitized infants.

This example illustrates the effect of LGG on the production of pro-inflammatory cytokines of splenic cells in subjects. To further assess whether the beneficial effect of maternal LGG supplementation on antibody production in offspring was associated with an immunological immune response related to immunological tolerance, mononuclear cells from spleen of OVA-sensitized and non-sensitized offspring were cultured in the presence of LGG or allergen (OVA). Cytokine production was assessed after 72 hours. Offspring from LGG-supplemented mouse mothers showed a significant reduced production of IFN-gamma, MCP-1, IL-10 and IL-6 (FIG. 6 A-D). These results indicate that the maternal LGG-exposure resulted in a significantly down-regulation of pro-inflammatory cytokines in these mice.

EXAMPLE 6

Figure 7:
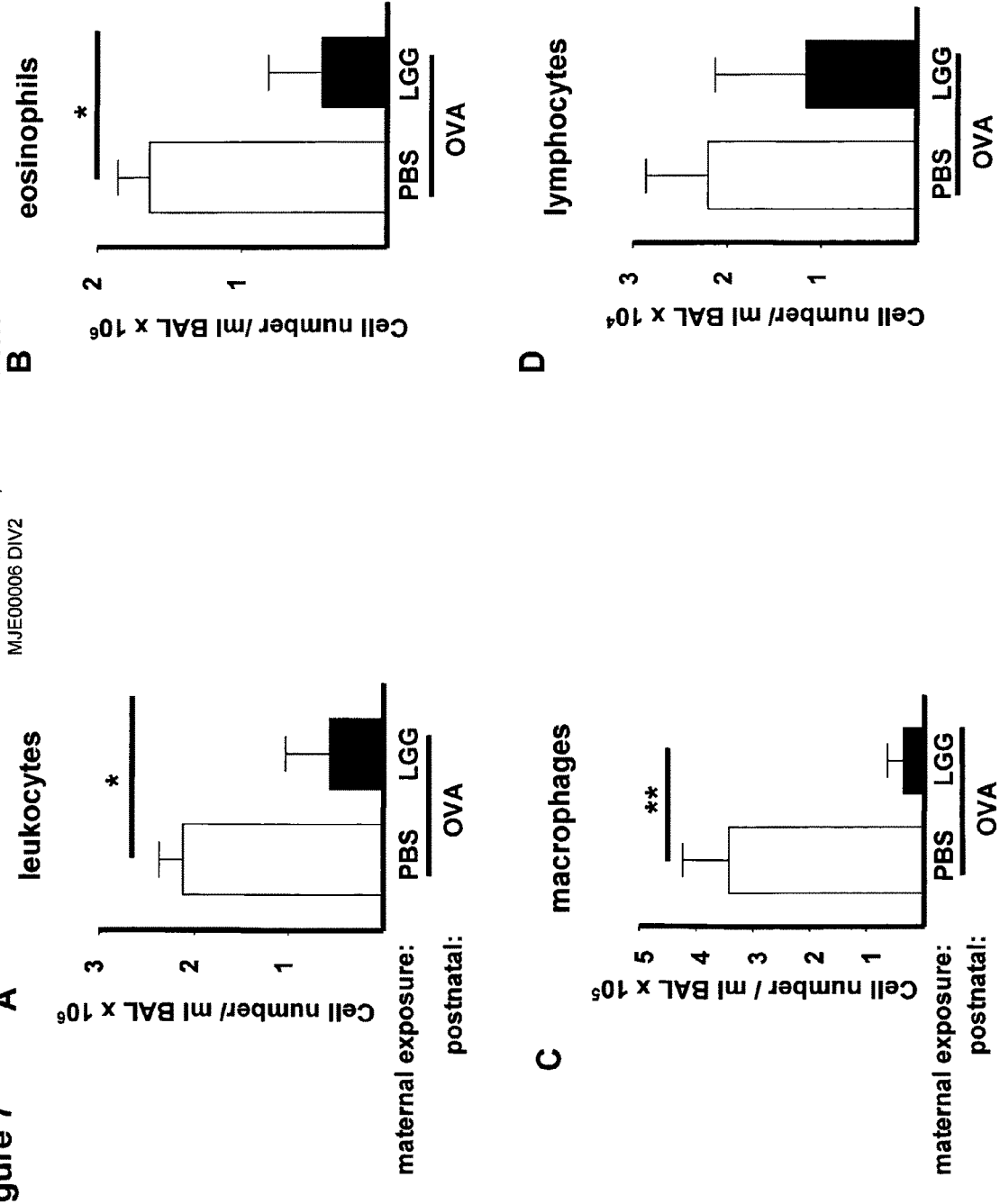
FIG. 7 illustrates the effect of LGG on the distribution of mononuclear cells in allergic airways.

This example illustrates the effect of LGG on the suppression of airway inflammation in allergic subjects. To test whether the effect of prenatal LGG-exposure influences the development of experimental asthma, OVA-sensitized mice were aerosol allergen-challenged four times. Airway inflammation was investigated by analyzing broncho-alveolar lavage (BAL) fluids. BAL fluids from OVA-sensitized mice from maternal LGG-exposed mothers contained significantly lower numbers of leukocytes as compared to OVA-sensitized mice prenatal exposed to PBS (FIG. 7). In addition, the cellular composition of BAL fluids showed a significant reduction of eosinophilic granulocytes as well as macrophages whereas lymphocytes only showed a tendency towards lower numbers.

EXAMPLE 7

This example describes the materials and methods necessary to show the effect of the prenatal and postnatal administration of LGG on the development of respiratory allergies and inflammation in the lung and airways. Female BALB/c mice received before mating to make BALB/c mice and during pregnancy i.g. LGG. The LGG supplementation was continued after delivery of the offspring during breast feeding until day 21 after delivery. Control mice received PBS instead of LGG.

Female BALB/c mice received 5 i.g. applications of $10^8$ cfu of freeze-dried LGG in a volume of 200 µl (reconstituted in PBS) on days 0, 2, 4, 6, 8, 10, and 12. Controls received PBS alone. On days 21 and 28 all animals received sensitizing i.p. injections of 100 µg cow's milk proteins together with 1.5 mg $Al(OH)_3$ adjuvant. To assess serum antibody levels and immunological effector function (PCA) blood was collected at days 0 and 49.

Wistar rats were shaven on the back and flanks and injected intradermally with 0.1 ml of the test sera in dilutions taken from the mice at day 49, followed 24 h later with an intravenous injection of 1 ml of a 1:1 mixture of a solution of cow's milk proteins (Mead Johnson Nutritionals, Evansville, Ind., USA) and solution of Evans blue (2% in sterile saline). After 20-30 min., the animals were examined for positive response. The diameter of dye extravasation at the site of the serum injection was measured.

Levels of cow's milk specific IgG1, IgG2a and IgE antibody titers were determined by ELISA technique at day 49. 96-well polystyrene flat-bottom microtiter plates (NUNC, Germany) were coated with cow's milk protein (5 µg/ml) diluted in 0.1 M carbonate coating buffer, pH 9.6, followed by 1 hour blocking (37° C.) with PBS/1% BSA/0.02 Tween 20. On each plate a reference curve generated with a positive pool serum (day 49 control) was determined (starting dilution 1:10 for IgE, 1:100 for IgG2a and 1:6400 for IgG1) a set at 1000 Arbitrary Units/ml (AU/ml) for specific Ag -specific Ab levels. For detection of IgE, IgG1 and IgG2a antibodies, PO-conjugated antibodies were added (1 hour at 37° C.). Subsequently, 3,3', 5,5'-tetramethylbenzidine (TMB; Sigma, Germany, 100 µl/well; 6 mg/ml DMSO) was used for the color reaction, which was stopped with 100 µl/well of 2N $H_2SO_4$ solution, and absorbance was measured at 450 nm. Cow's milk specific antibody titers were expressed as arbitrary uints (AU) in comparison to the reference serum.

Blood was collected before and 1 hour after an oral challenge with 100 mg cow's milk proteins/animal at day 56 and seum levels of mmcp-1 were determined with an ELISA kit (Moredun, Scotland). The ELISA was performed according to the manufacturer's instructions. Data was analyzed using the GraphPad Prism software, Version 3.02. Differences between group means were determined by using a Mann Whitney-U test. Values of $p<0.05$ were considered statistically significant.

EXAMPLE 8

This example illustrates the presence of LGG in the feces of mice treated prenatally and postnatally with LGG. The presence of LGG was assessed in fecal samples from LGG-treated mice versus mice which received PBS only. After microbial culturing, LGG was present in fecal samples from LGG-treated mice, whereas no LGG could be detected in PBS-treated mice. To further confirm that the detected LGG is indeed identical with the LGG supplementation, DNA was prepared from fecal samples and amplified with LGG-PCR-specific primers. As shown in FIG. 1B, LGG specific PCR products could be detected in the samples from LGG-treated mice whereas no LGG-specific PCR products were detectable in samples from PBS-treated mice. This result indicates that pre- and early postnatal treatment of mice resulted in colonization of the gut and LGG is still detectable at least three weeks after the last LGG supplementation.

To assess whether maternal LGG treatment resulted in LOG colonization of the neonates, DNA was prepared from fecal samples from neonates at the age of 53 days. The PCR analysis revealed that neither PBS-treated nor LGG-treated mice were colonized with LGG. This result indicates that the maternal-delivered LGG is not transmitted to the neonates during the prenatal or postnatal period.

To further assess whether the pre- and early postnatal LGG-supplementation impacts the distribution of the bacterial gut colonization, several bacterial strains (LGG, *Enterococcus, E. coli, Staphylococcus aureus, Bacteriodes*) were assessed in fecal samples. There was a tendency that LGG-supplementation alters the bacterial colonization in a beneficial way. Bacteria of the species *Enterococcus, E. coli*, and *Bacteriodes* were detected in higher numbers in the fecal samples from LGG-supplemented mice when compared to control mice. In addition, there was a tendency of reduced *Staphylococcus aureus* colonization in the gut of LGG-treated mice when compared to PBS-treated mice. These results indicate that LGG treatment may improve the normal health gut colonization and also hinder the proliferation of pathological bacteria in the mouse gut.

EXAMPLE 9

This example illustrates the effect of pre- and early postnatal LGG supplementation on the production of serum allergen-specific antibodies in allergic neonates versus control. Allergen-specific antibody production was assessed in neonates after i.p. sensitization to OVA following OVA-allergen aerosol exposure. Maternal LOG supplementation hinders the development of an allergen-specific antibody response as indicated by a significant reduced production of anti-OVA IgG1 in pre- and early postnatal LGG-treated mice, compared to PBS controls. The murine IgG1 antibody subclass is the human equivalent of IgE antibody. This is the effector molecule in allergic manifestations such as positive skin prick tests and development of airway inflammation. The level of anti-OVA IgG2a antibody production was significantly different between LGG-treated mice and PBS-treated mice. These results indicate that maternal LGG-supplementation reduces allergic sensitization to an allergen later in life.

EXAMPLE 10

This example illustrates the effect of pre- and early postnatal LGG supplementation on the production of serum IgA antibodies in allergic neonates versus control. Breast milk contains high levels of secretory antibodies of the subclass IgA. It is also well known that this antibody subclass is associated with the development of immunological tolerance after allergen exposure. Therefore, the result that there was a significant increase in serum IgA antibody production in neonates from LGG-supplemented mothers compared to neonates from control mothers (PBS) was surprising. This result clearly indicates that maternal LGG-supplementation not only hinders the development of an allergic immune response in neonates as indicated by a significantly decreased production of IgG1 antibodies, but also induces a pattern of antibody production (IgA) which is associated with the development of immunological tolerance.

EXAMPLE 11

This example illustrates the effect of pre- and early postnatal LGG supplementation on the production of pro-inflammatory cytokines in allergic neonates versus control. Mononuclear cells from spleen of OVA-sensitized and non-sensitized neonates were cultured in the presence of LGG or allergen (OVA). Cytokine production was assessed after 72 hours. Neonates from LGG-supplemented mothers showed a significant reduced production of IFN-gamma, MCP-1, IL-10 and IL-6. These results indicate that the maternal LGG-exposure resulted in a significantly down-regulation of pro-inflammatory cytokines in these neonates.

EXAMPLE 12

This example illustrates the effect of pre- and early postnatal LGG supplementation on the suppression of airway inflammation in allergic neonates versus control. OVA-sensitized mice were aerosol allergen challenged four times. Airway inflammation was investigated by analyzing broncho-alveolar lavage (BAL) fluids. BAL fluids from OVA-sensitized mice from maternal LGG-exposed mothers contained significantly lower numbers of leukocytes as compared to OVA-sensitized mice that were prenatally exposed to PBS ($p<0.05$). In addition, the cellular composition of BAL fluids showed a significant reduction of eosinophilic granulocytes as well as macrophages ($p<0.05$) whereas lymphocytes only showed a tendency towards lower numbers.

EXAMPLE 13

This example illustrates the effect of postnatal LGG supplementation on the development of an allergic phonotype later in life. To assess the impact of postnatal LGG exposure on the development of an allergic phenotype later in life, female BALB/c mice received either LGG or PBS saline for two weeks (day 14). At day 21 and 28, the mice received two sensitizing injections of cow's milk proteins. On day 49 and 56, production of cow's milk specific antibodies (FIG. 8) and immunological effector function, such as passive cutaneous anaphylaxis test (FIG. 9A) and serum mast cell protease-1 release after oral challenge (FIG. 9B), were assessed.

Figure 8:
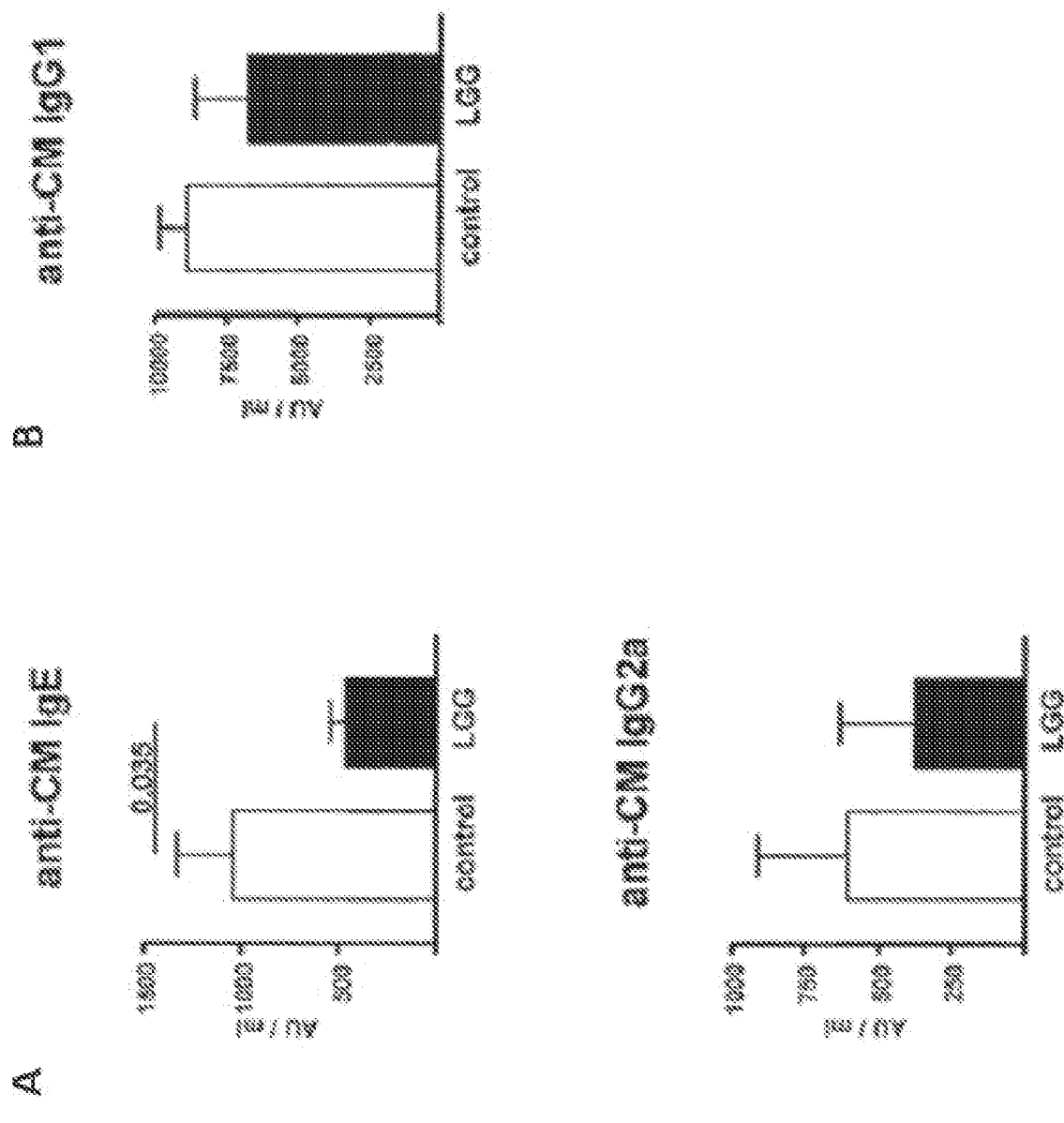
FIG. 8 illustrates the suppression of cow's milk specific antibody production, anti-CM IgE (FIG. 8A), anti-CM IgG1 (FIG. 8B), and anti-CM IgG2a (FIG. 8C).
Figure 9:
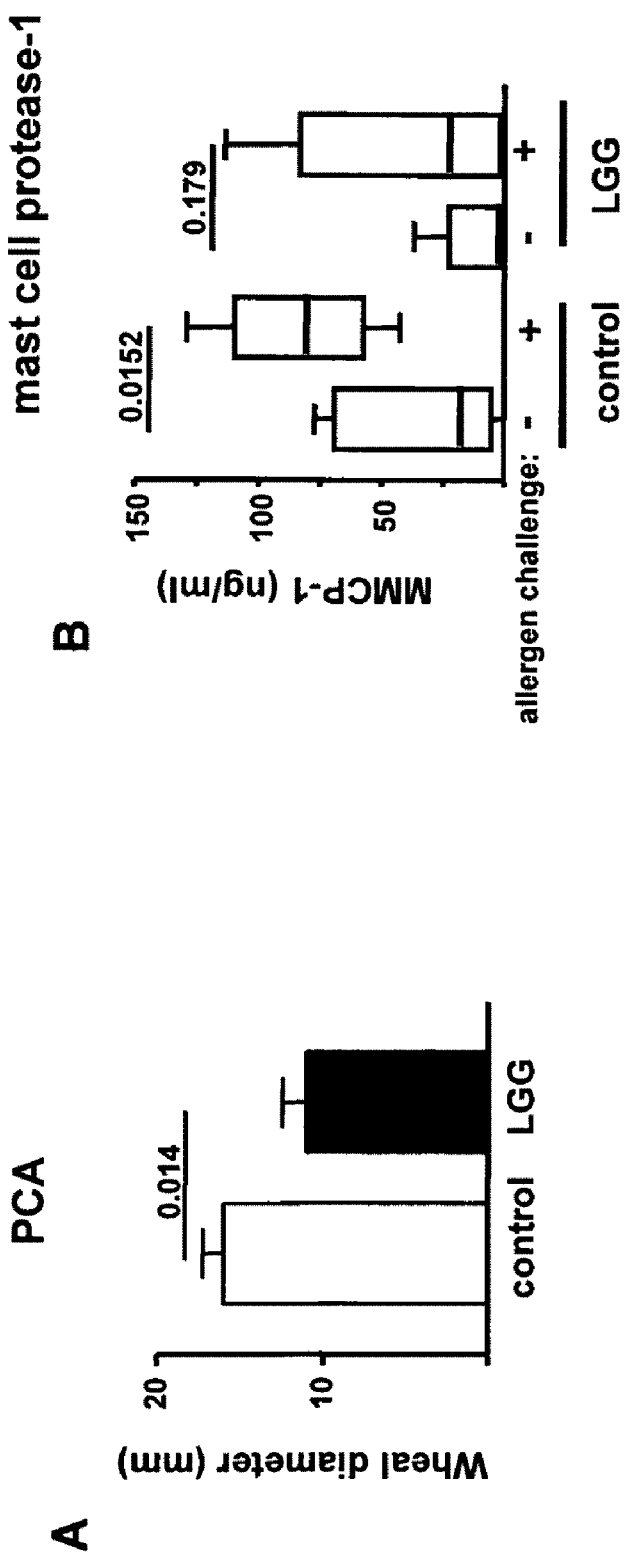
FIG. 9 illustrates the assessment of immunological effector function of cow's milk specific antibodies by passive cutaneous anaphylaxis test (FIG. 9A) and mast cell protease-I release assay (FIG. 9B).

As shown in FIG. 8, postnatal LGG supplementation hinders the development of an allergen specific antibody response as indicated by a significant reduced production of cow's milk specific IgE antibodies. The reduced production of allergen-specific IgE antibodies was associated with significantly smaller wheal and flare reactions after allergen-challenge (FIG. 9A). The reduced production of allergen-specific IgE antibodies was also associated with significantly reduced release of mast cell protease-1 after allergen-challenge (FIG. 9B). These results indicate that the LGG supplementation reduces the development of an allergen-specific immune response and also reduces allergic symptoms after allergen exposure. Thus, LGG exposure before allergic sensitization reduces the development of an allergic phenotype later in life.

All references cited in this specification, including without limitation, all papers, publications, patents, patent applications, presentations, texts, reports, manuscripts, brochures, books, internet postings, journal articles, periodicals, and the like, are hereby incorporated by reference into this specification in their entireties. The discussion of the references herein is intended merely to summarize the assertions made by their authors and no admission is made that any reference constitutes prior art. Applicants reserve the right to challenge the accuracy and pertinence of the cited references.

These and other modifications and variations to the present invention may be practiced by those of ordinary skill in the art, without departing from the spirit and scope of the present invention, which is more particularly set forth in the appended claims. In addition, it should be understood that aspects of the various embodiments may be interchanged in whole or in part. Furthermore, those of ordinary skill in the art will appreciate that the foregoing description is by way of example only, and is not intended to limit the invention so further described in such appended claims. Therefore, the spirit and scope of the appended claims should not be limited to the description of the preferred versions contained therein.

What is claimed is:

1. A method for preventing or treating allergy-induced inflammation in the lung and airways of an infant, the method comprising prenatally administering and/or postnatally administering to the infant an effective amount of *Lactobacillus* GG prior to allergic sensitization of the infant.

2. The method of claim 1, wherein the prenatal administration of *Lactobacillus* GG comprises ingestion of *Lactobacillus* GG by the pregnant mother of the unborn infant.

3. The method of claim 1, wherein the postnatal administration of *Lactobacillus* GG comprises ingestion of *Lactobacillus* GG by the infant's mother followed by breast feeding of the infant by the mother.

4. The method of claim 1, wherein the postnatal administration of *Lactobacillus* GG comprises incorporation of the *Lactobacillus* GG into an infant formula and consumption of the formula by the infant.

5. The method of claim 1, wherein the amount of *Lactobacillus* GG administered to the infant is between about $1 \times 10^4$ and $1 \times 10^{12}$ cfu/L/kg/day.

6. The method of claim 1, wherein the amount of *Lactobacillus* GG administered to the infant is between about $1 \times 10^6$ and $1 \times 10^9$ cfu/L/kg/day.

7. The method of claim 1, wherein the method further comprises administering to the infant at least one probiotic.

8. The method of claim 1, wherein the method further comprises administering to the infant at least one prebiotic.

9. A method for decreasing mucus production in the airway of an infant, the method comprising prenatally administering and/or postnatally administering to the subject an effective amount of *Lactobacillus* GG prior to allergic sensitization of the infant.

10. The method of claim 9, wherein the prenatal administration of *Lactobacillus* GG comprises ingestion of *Lactobacillus* GG by the pregnant mother of the unborn infant.

11. The method of claim 9, wherein the postnatal administration of *Lactobacillus* GG comprises ingestion of *Lactobacillus* GG by the infant's mother followed by breast feeding of the infant by the mother.

12. The method of claim 9, wherein the postnatal administration of *Lactobacillus* GG comprises incorporation of the *Lactobacillus* GG into an infant formula and consumption of the formula by the infant.

13. The method of claim 9, wherein the amount of *Lactobacillus* GG administered to the infant is between about $1 \times 10^4$ and $1 \times 10^{12}$ cfu/L/kg/day.

14. The method of claim 9, wherein the amount of *Lactobacillus* GG administered to the infant is between about $1 \times 10^6$ and $1 \times 10^9$ cfu/L/kg/day.

15. The method of claim 9, wherein the method further comprises administering to the infant at least one probiotic.

16. The method of claim 9, wherein the method further comprises administering to the infant at least one prebiotic.

* * * * *